United States Patent
Fliedner

(10) Patent No.: US 8,628,563 B2
(45) Date of Patent: Jan. 14, 2014

(54) SUPPORT PROSTHESIS

(75) Inventor: Thilo Fliedner, Munich (DE)

(73) Assignee: Thilo Fliedner (DE)

( * ) Notice: Subject to any disclaimer, the term of this patent is extended or adjusted under 35 U.S.C. 154(b) by 781 days.

(21) Appl. No.: 11/687,483

(22) Filed: Mar. 16, 2007

(65) Prior Publication Data

US 2007/0239263 A1    Oct. 11, 2007

Related U.S. Application Data

(63) Continuation of application No. PCT/DE2005/001635, filed on Sep. 16, 2005.

(30) Foreign Application Priority Data

Sep. 17, 2004   (DE) .......................... 10 2004 045 226

(51) Int. Cl.
   *A61F 2/06*   (2013.01)

(52) U.S. Cl.
   USPC ....................................................... 623/1.15

(58) Field of Classification Search
   USPC ................... 623/1.15, 1.17, 1.22, 1.12, 1.16, 623/1.18–1.2
   See application file for complete search history.

(56) References Cited

U.S. PATENT DOCUMENTS

| | | | |
|---|---|---|---|
| 5,922,020 A * | 7/1999 | Klein et al. ................... | 623/1.15 |
| 6,398,805 B1 | 6/2002 | Alt | |
| 6,423,090 B1 * | 7/2002 | Hancock ...................... | 623/1.15 |
| 6,461,381 B2 | 10/2002 | Israel et al. | |
| 7,258,697 B1 * | 8/2007 | Cox et al. .................... | 623/1.16 |
| 2002/0055770 A1 * | 5/2002 | Doran et al. ................. | 623/1.15 |
| 2002/0068969 A1 * | 6/2002 | Shanley et al. .............. | 623/1.16 |
| 2002/0123799 A1 | 9/2002 | Burgermeister | |
| 2002/0138131 A1 * | 9/2002 | Solovay et al. .............. | 623/1.15 |
| 2002/0165602 A1 * | 11/2002 | Douglas et al. ............. | 623/1.13 |
| 2002/0183831 A1 * | 12/2002 | Rolando et al. ............. | 623/1.15 |
| 2004/0117002 A1 * | 6/2004 | Girton et al. ................ | 623/1.16 |
| 2004/0225350 A1 * | 11/2004 | Shanley ....................... | 623/1.16 |
| 2006/0009837 A1 * | 1/2006 | Burgermeister et al. .... | 623/1.15 |

FOREIGN PATENT DOCUMENTS

| | | |
|---|---|---|
| DE | 29521206 U1 | 9/1996 |
| DE | 19653721 A1 | 4/1998 |
| DE | 19653709 A1 | 7/1998 |
| DE | 29816878 U1 | 12/1998 |
| DE | 19834956 A1 | 5/1999 |
| DE | 10153340 A1 | 11/2002 |
| DE | 10144430 A1 | 3/2003 |
| DE | 69532049 T2 | 7/2004 |
| EP | 0 910 998 | 4/1999 |
| EP | 1 374 802 | 1/2004 |
| WO | 9526695 A2 | 10/1995 |
| WO | 9603092 A1 | 2/1996 |

(Continued)

OTHER PUBLICATIONS

International Search Report, Dec. 13, 2005, 2 pages.

(Continued)

*Primary Examiner* — Thomas McEvoy
(74) *Attorney, Agent, or Firm* — St. Onge Steward Johnston & Reens LLC

(57) ABSTRACT

A uniformly expandable support prosthesis has bending curves which taper in the region of curvature toward a narrowing. This allows uniform bending of the bending curves along the individual support rings.

12 Claims, 4 Drawing Sheets

(56) References Cited

FOREIGN PATENT DOCUMENTS

| WO | 98/05270 | 2/1998 |
| WO | 9858600 A1 | 12/1998 |
| WO | 02094127 A2 | 11/2002 |
| WO | 2004/058104 | 7/2004 |

OTHER PUBLICATIONS

European Office Action; Application No. EP 05 792 405.2; Aug. 5, 2010; 4 pages.

* cited by examiner

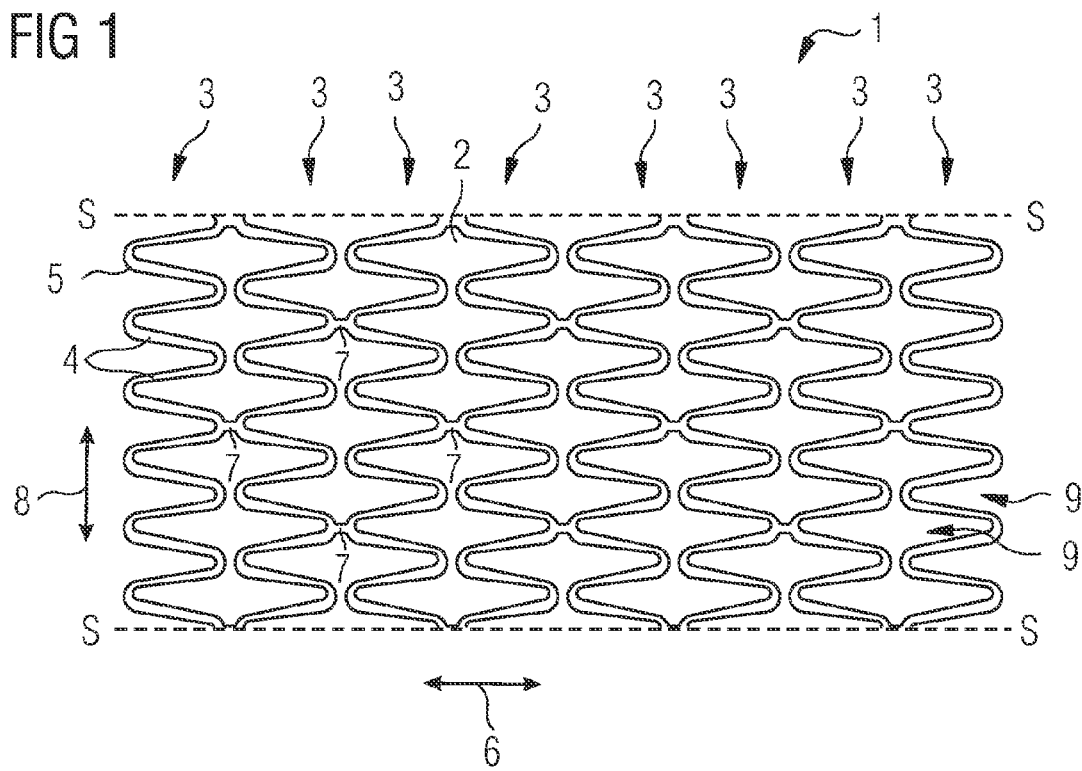
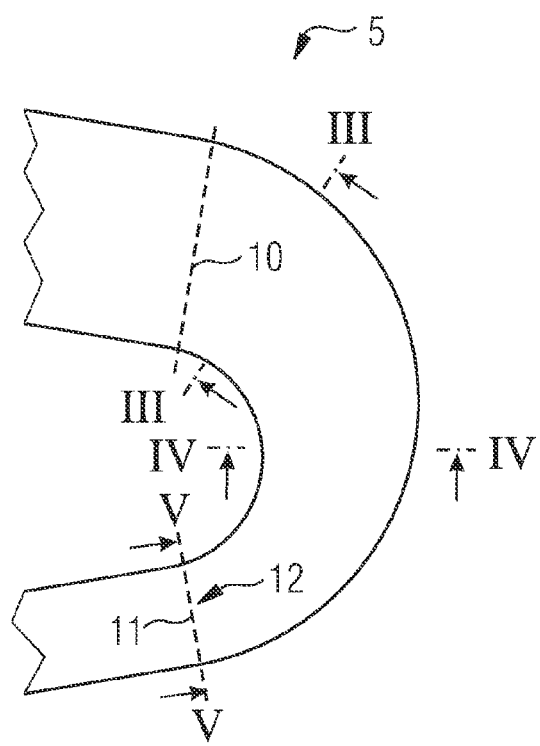
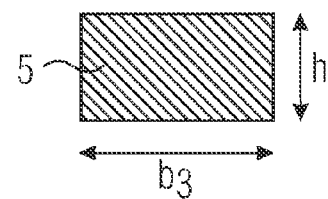
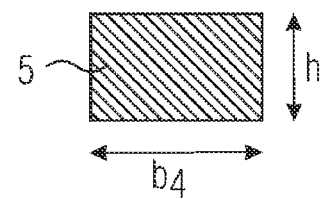
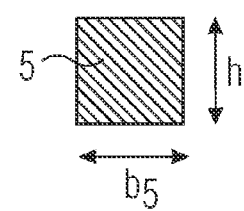

SUPPORT PROSTHESIS

CROSS-REFERENCE TO RELATED APPLICATIONS

The present application is a continuation of pending International patent application PCT/DE2005/001635 filed on Sep. 16, 2005 which designates the United States and claims priority from German patent application 10 2004 045 226.1 filed on Sep. 17, 2004, the content of which is incorporated herein by reference.

FIELD OF THE INVENTION

The invention relates to a support prosthesis for vessels or intracorporeal lumens with a tubular casing having an expandable meandering pattern which is formed by a filament and has a respective narrowing in a large number of bending curves.

BACKGROUND OF THE INVENTION

A support prosthesis of this type, referred to as a stent, is known from EP 1 374 802 A1. The known stent has a tubular casing with a large number of meandering support rings which are connected by connecting elements extending substantially in the longitudinal direction and having a large number of loops. The curve portions of the meandering support rings can be tapered beyond the entire bending curve to facilitate bending of the bending curves. However, the bending curves must not be weakened to the extent that the strength of the support rings is threatened in the stretched state.

The known stent is conventionally attached to a balloon catheter and brought by means of the balloon catheter into the region of the vessel to be widened. This can, for example, be a stenosis in the region of a coronary vessel. Inflating the balloon catheter then causes the stent to be expanded in the radial direction to such an extent that the support rings experience plastic deformation. The support rings hold the vessel in a widened state even after the balloon catheter has been withdrawn.

On expansion of the stent, it is advantageous if the stent expands uniformly such that the bending curves provided for the plastic deformation deform as uniformly and simultaneously as possible, so the vessel to be widened is loaded uniformly.

Starting from this prior art, the object of the invention is therefore to provide a uniformly expandable support prosthesis.

SUMMARY OF THE INVENTION

This object is achieved by a support prosthesis having the features recited in the independent claim. Claims dependent thereon recite advantageous embodiments and developments.

The support prosthesis for vessels or intracorporeal lumens has a tubular casing with an expandable meandering pattern which is formed by a filament and the bending curves of which respectively taper within the bending curve to a narrowing having a minimum cross-sectional area and the bending curves of which can stretch by deformation extending from the smallest cross-sectional area to larger cross-sectional areas.

The term "bending curve" refers to a curve of the meandering pattern extending between straight portions or turning points of the meandering pattern.

On expansion of the support prosthesis by the balloon catheter, the meandering patterns are stretched uniformly as, on tensile loading of the meandering pattern, the deformation of the bending curves starts almost simultaneously at the respective narrowings and then proceeds continuously into the regions of the bending curves having a larger cross-sectional area than the respective narrowing. In particular, the continuous tapering of the bending curves toward the narrowing prevents the stretching movement of the meandering pattern from leading initially to the stretching of individual bending curves, as complete stretching of one bending curve is preceded by the deformation of an adjacent bending curve at the narrowing. This allows uniform expansion of the support prosthesis.

In one embodiment, the bending curves are free from portions having a constant cross-sectional area. This promotes a uniform stretching process.

In a preferred embodiment, the narrowing is located remote from the curve centre of each bending curve. In a configuration of this type, a particularly large maximum cross-sectional area to minimum cross-sectional area ratio can be produced within the bending curve. It is to be expected that the meandering pattern stretches particularly uniformly on expansion of the stent.

In a further preferred embodiment, the bending curve has merely a single narrowing. For in this configuration, deformation starts in a predictable manner at a defined location and then continues into the thicker portions of the bending curve.

BRIEF DESCRIPTION OF THE DRAWINGS

Further details and advantages of the invention emerge from the following description in which embodiments of the invention are described in detail with reference to the appended drawings, in which:

FIG. 1 is a plan view onto a cut-open stent with a large number of support rings extending in meandering form in the circumferential direction;

FIG. 2 is an enlarged view of a bending curve of one of the meandering support rings from FIG. 1;

FIG. 3 is a cross section through the curvature portion from FIG. 2, taken along the sectional line III-III;

FIG. 4 is a cross section through the curvature portion from FIG. 2, taken along the sectional line IV-IV;

FIG. 5 is a cross section through the curvature portion from FIG. 2, taken along the sectional line V-V;

DETAILED DESCRIPTION OF THE INVENTION

Figure 6:
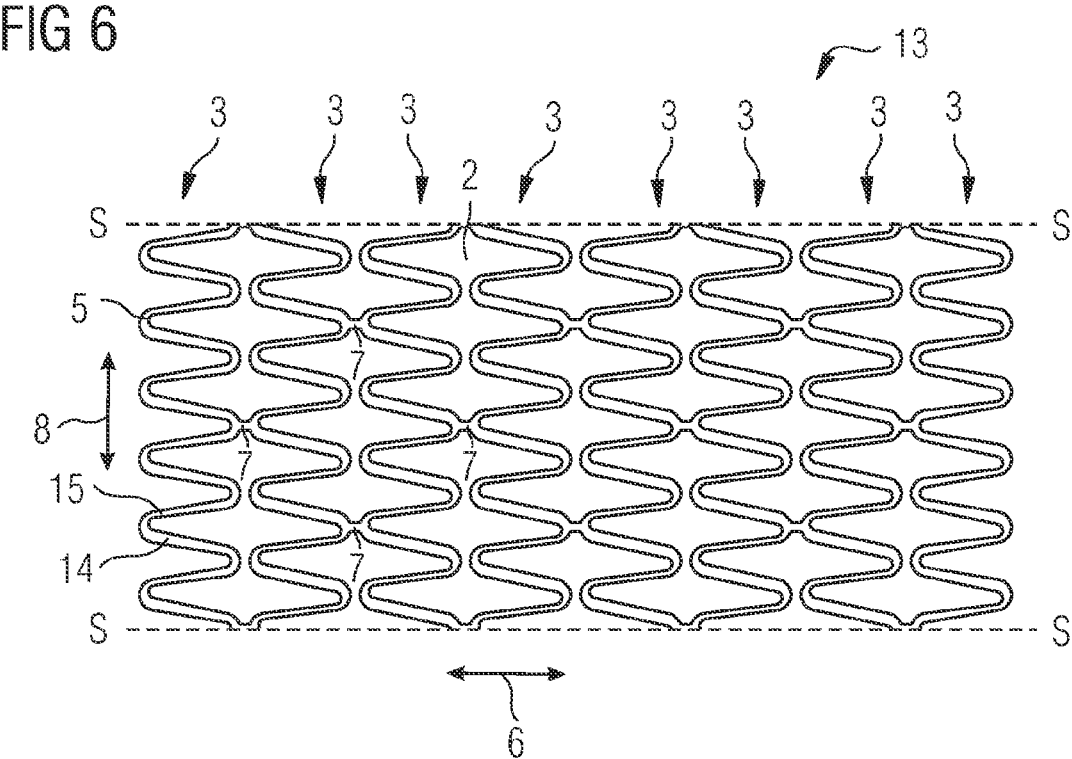
FIG. 6 is a plan view onto a further cut-open stent with a large number of support rings meandering in the circumferential direction.

FIG. 1 is a plan view onto a stent 1 with a tubular casing 2. The stent 1 is shown such as it would appear cut open along a sectional line S-S and resting flat on a planar surface. The stent 1 has a number of meandering support rings 3 composed of a large number of substantially rectilinear support struts 4 connected via bending curves 5.

The support rings 3 are connected by connecting elements 7 in a longitudinal direction 6. As the meandering course of adjacent support rings is, in each case, phase-offset through 180°, the connecting elements 7 extending between adjacent bending curves 5 can be kept short. However, use can also be made of connecting elements 7 having a meandering course in the longitudinal direction 6. Nevertheless, this is not absolutely crucial, as at least two bending curves 5 without connecting elements 7 are located along the support rings 3 between two bending curves 5 with connecting elements 7. Any other even number of bending curves 5 without connecting elements 7 can also be located between the connecting elements 7. It two bending curves 5 without connecting elements 7 are located, in each case, between two connecting elements 7, the support rings 3 between two respective connecting elements 7 each have an N-shaped course. As a result, the stent 1 is sufficiently flexible even when conveyed through narrowly curved vessels.

For conveyance through a vessel, the tubular stent 1 is attached to a balloon catheter. On expansion of the balloon catheter, the cylindrical stent 1 is expanded in the radial direction. The support rings 3 are, in this case, stretched in a circumferential direction 8. The bending curves 5 are then configured in such a way that the stretching movement takes place as uniformly as possible. In particular, individual loops 9 formed by a respective bending curve 5 and the adjacent support struts 4 are to be stretched both as uniformly and as simultaneously as possible.

The term "simultaneous stretching of the bending curves 5" refers to stretching that does not necessarily take place at the same time, but that has a time overlap. For in practice, frictional forces between the stent 1 and the balloon catheter can cause the bending curves 5 to stretch in a time-offset manner.

FIG. 2 is an enlarged view of one of the bending curves 5. FIGS. 3 to 5 are cross sections through the bending curve 5 from FIG. 2. FIG. 2 to 5 show that the bending curve 5, which extends between interfaces 10 and 11 indicated by broken lines in FIG. 2, tapers toward a narrowing 12.

The reduction in cross section from the interface 10 to the interface 11 can be seen particularly clearly from FIGS. 3 to 5.

The stent 1 is preferably made from a metal pipe. The support rings 3 and the connecting elements 7 are, in this case, machined from the metal pipe using a laser. The cross sections shown in FIGS. 3 to 5 thus each have the same height h along the sectional lines III-III, IV-IV and V-V. However, the cross-sectional areas differ with regard to width. In particular, for the respective widths $b_3$, $b_4$ and $b_5$, the following applies: $b_3 > b_4 > b_5$.

The width of the bending curve 5 can be reduced in the region of the narrowing 12 to such an extent that the width $b_5$ of the bending curve 5 in the narrowing 12 is less than the height h.

As stated hereinbefore, on expansion of the stent 1, expansion of the balloon catheter located inside the stent 1 causes the support rings 3 to stretch. The stretching of the support rings 3 in the circumferential direction 8 is brought about by deformation of the bending curves 5. The deformation of the bending curves 5 begins at the narrowing 12 which has the minimum cross-sectional area within the bending curve 5. The deformation embrittles the region around the narrowing 12. With increasing stretching of the support rings 3, the deformation of the bending curves 5 therefore continues in the direction of the interface 10. An increasing amount of deformation work must be performed in this case. Almost complete stretching of a bending curve 5 will therefore be preceded by the deformation of an adjacent bending curve 5. It is therefore to be expected that the loops 9 of the support rings 3 will be stretched uniformly and simultaneously.

For uniform opening of the support rings 3, it is advantageous if each of the bending curves 5 has a narrowing 12. The narrowings 12 may, as shown in FIG. 1, be arranged with respect to the circumferential direction exclusively on the inlet side or the outlet side in the respective bending curves 5.

FIG. 6 shows a further stent 13 in which the narrowings 12 are arranged alternately on the inlet side and on the outlet side in the bending curves 5. Wide support struts 14 and narrow support struts 15 therefore alternate in a support ring 3. The narrow support struts 15 can, if appropriate, act resiliently if portions of a support ring 3 catch in the vessel wall on expansion.

Figure 7:
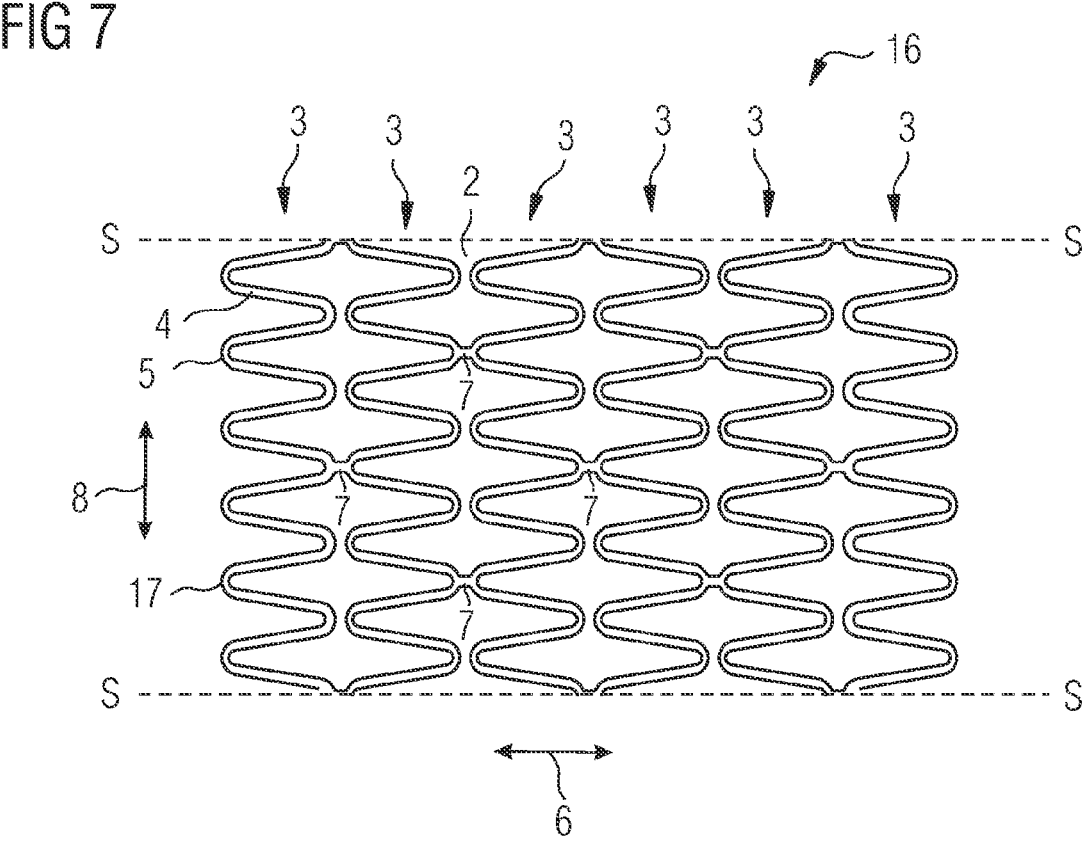
FIG. 7 is a plan view onto a cut-open stent, the meandering support rings of which each have a narrowing arranged in the region of the curve centre of the bending curves.

FIG. 7 shows a further stent 16, the bending curves 17 of which each have a narrowing 18 in the region of a centre line 19 of the bending curve 17.

Figure 8:
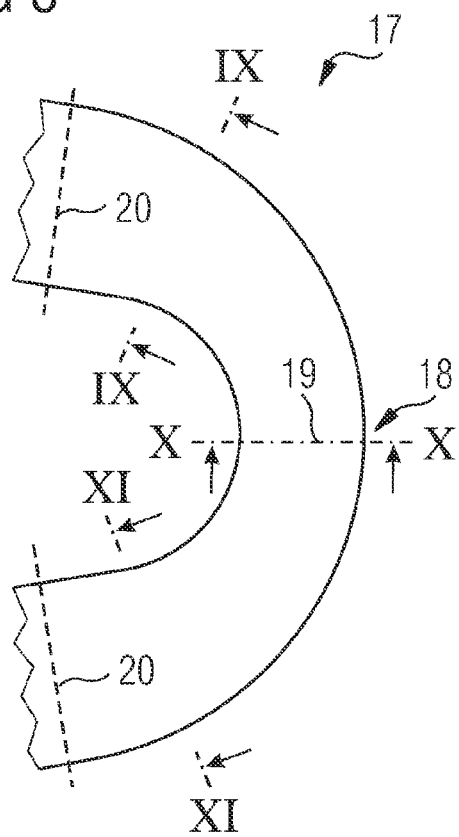
FIG. 8 is an enlarged view of a bending curve of the stent from FIG. 7.
Figure 9:
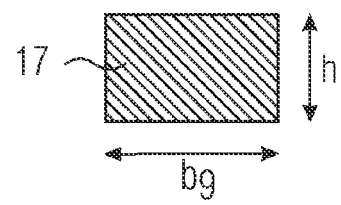
FIG. 9 is a cross section through the bending curve from FIG. 8, taken along the sectional line IX-IX.
Figure 10:
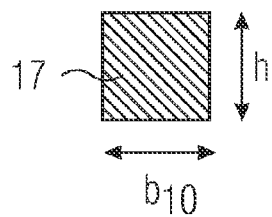
FIG. 10 is a cross section through the bending curve from FIG. 8, taken along the sectional line X-X.
Figure 11:
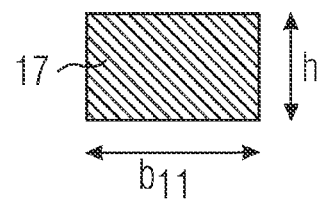
FIG. 11 is a cross section through the bending curve from FIG. 8, taken along the sectional line XI-XI.

FIG. 8 is an enlarged view of one of the bending curves 17. FIG. 9 to 11 are sections through the bending curve 17 from FIG. 8, taken along the sectional lines IX-IX, X-X and XI-XI. The height h of the cross-sectional areas shown in FIGS. 9 to 11 is identical in each case, merely the widths $b_9$, $b_{10}$ and $b_{11}$ differ. In particular, the following applies: $b_{10} < b_9$, $b_{11}$.

On deformation of the stent 16, the bending curves 17 are stretched. The deformation of the bending curves 17 begins, in each case, at the narrowing 18 and continues in both directions toward interfaces 20 of the bending curves 17. An increasing amount of deformation work must be performed in this case, so the bending curves 17 of a support ring 3 bend almost simultaneously. For complete stretching of one of the bending curves 17 is preceded by the deformation of adjacent bending curves at the narrowing 18.

Figure 12:
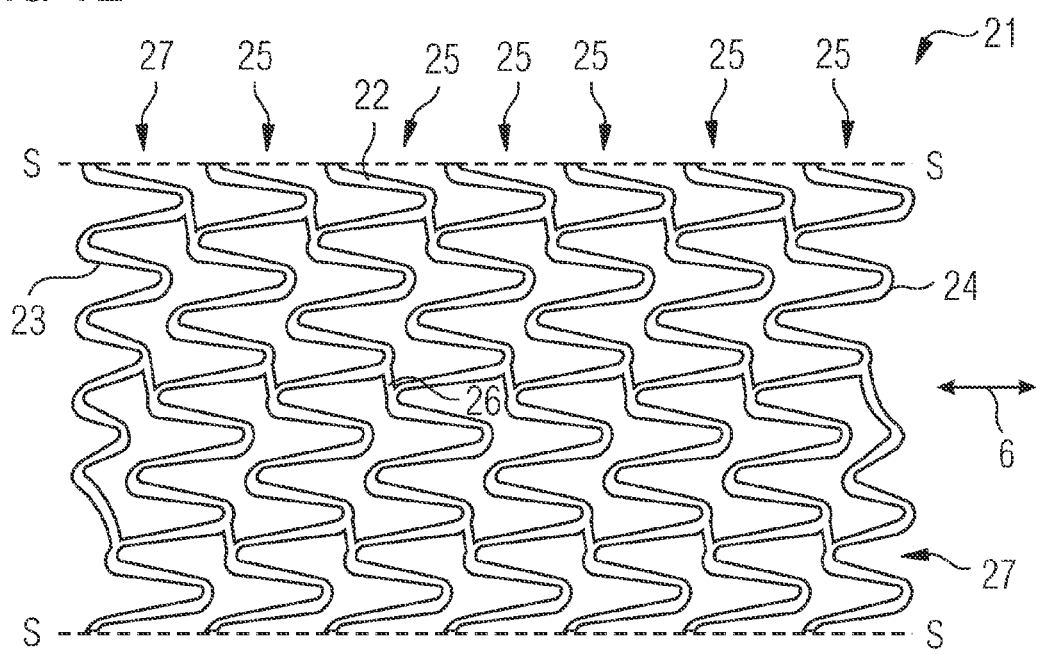
FIG. 12 is a plan view onto a cut-open stent in which the meandering pattern follows a helix path.

FIG. 12 shows a stent 21 which is cut open along the sectional line S-S and has a meandering support helix 22. The support helix 22 has, in this case, almost rectilinear support struts 23 which are connected via bending curves 24. Furthermore, helix paths 25 located next to one another are connected by connecting elements 26 extending in the longitudinal direction 7. At the ends of the stent 21, the support helix 22 forms loops 27 in each case.

The stent 21 is an example of a stent in which the supporting force is applied not by support rings arranged next to one another but rather by a support helix 22. The concept of weakening the bending curves 24 can be used also in the case of a stent 21 of the type of the stent shown in FIG. 12. The bending curves 24 can thus have a form corresponding to the bending curves 5 or 17.

The configuration of the bending curves can also be modified.

Figure 13:
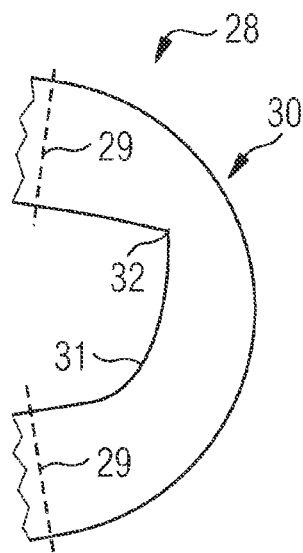
FIG. 13 is an enlarged view of a bending curve of a stent, the inner curve of which has differing radii of curvature.

FIG. 13 shows a bending curve 28 extending between interfaces 29. The bending curve 28 has a narrowing 30 formed by a notching 32 provided in an inner curve 31 of the bending curve 28. In practice, the notching 32 does not have any sharp corners, as the stents are generally subjected to a final electropolishing process which rounds off sharp edges and corners. In practice, it is therefore the case that the curvature of the inner curve 28 rises abruptly in the region of the narrowing 32.

A drawback of a bending curve 28 of the type shown in FIG. 13 is that cracks can form in the region of the notching 32. However, the targeted weakening at specific points, on the other hand, allows the bending curves 28 to deform almost simultaneously.

Figure 14:
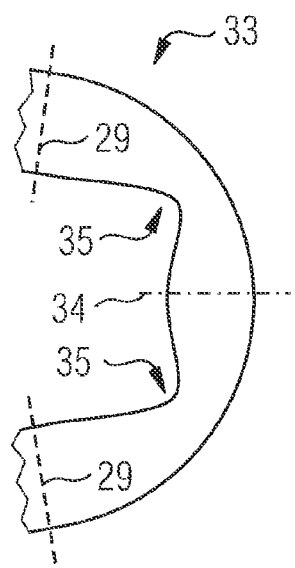
FIG. 14 is an enlarged view of a bending curve with two narrowings.

FIG. 14 shows a further bending curve 33 having two narrowings 35 arranged remote from a centre line 34. The bending curve 33 has, to a certain extent, two points of articulation which can deform on deformation of the bending curve 33.

Figure 15:
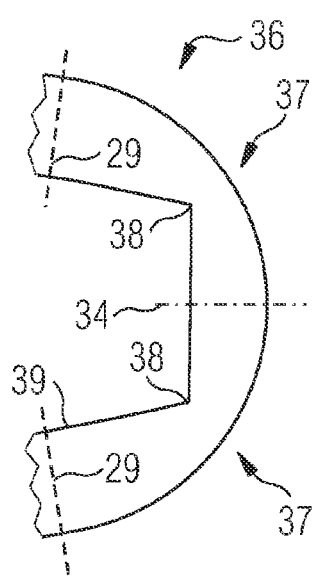
FIG. 15 is an enlarged view of a bending curve with two narrowings, the inner curve of which has differing radii of curvature in the region of the narrowings.

FIG. 15 shows a bending curve 36 which also has, remote from the centre line 34, narrowings 37 formed by notches 38 provided in an inner curve 39 of the bending curve 36.

Figure 16:
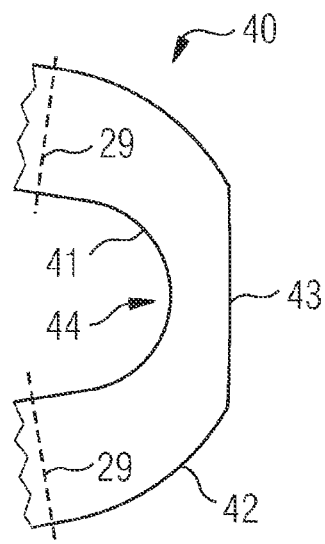
FIG. 16 is an enlarged view of a bending curve, the outer curve of which has a flat portion.

Finally, FIG. 16 shows a bending curve 40 with an inner curve 41 of continuous curvature and an outer curve 42 having a flat portion 43 forming a narrowing 44.

The stents 1, 13 and 16 described in the present text have support rings 3, the bending curves 5, 17, 24, 28, 33, 36 and 40 of which are bent simultaneously and uniformly on expansion of the stents 1, 13 and 16. Loading of the vessel walls at specific points is thus avoided.

It should be noted that the narrowings 12 and 18 can extend along a bending curve. It is to be expected that the bending curves 5 and 17 will stretch uniformly even if the narrowings 12 and 18 extend over approximately 25%, in some cases even over 50%, of the curve length of the bending curves 5 and 17. Nevertheless, it is to be expected that the bending curves 5 and 17 will stretch particularly uniformly if the narrowings 12 and 18 extend over less than 10%, preferably 5% of the curve length of the bending curves 5 and 17.

Those portions in which the bending curves 5, 17, 24, 28, 33, 36 and 40 taper should accordingly extend over as large an area as possible of the bending curves 5, 17, 24, 28, 33, 36 and 40 in order to facilitate as complete and uniform stretching of the bending curves 5, 17, 24, 28, 33, 36 and 40 as possible. The tapering region should in this case extend over at least 50% of the curve length, advantageously over 75%, preferably over 90% or even over 95% of the curve length.

Advantageously, the bending curves are, as shown in FIG. 1 to 16, free from portions having a constant cross-sectional area. This promotes uniform and simultaneous stretching of the bending curves 5, 17, 24, 28, 33, 36 and 14. Uniform and simultaneous stretching is further promoted if, as in the embodiments of FIGS. 1 to 12, merely a single narrowing is provided in the bending curves 5, 17.

Irrespective of this, the bending curves 5, 17, 24, 28, 33, 36 and 40 can in principle, in the embodiments shown in the present text, be fully stretched.

The invention claimed is:

1. A support prosthesis for vessels or intracorporeal lumens with a tubular casing having an expandable meandering pattern forming one or more support rings and which is formed by a filament having successive bending curves that are bent alternatively in opposite directions and that are to be stretched on expansion of the support prosthesis by reducing the curvature of the bending curves, wherein all of said bending curves have a respective narrowing in which the cross sectional area of the filament is at its minimum, and wherein the cross-sectional area of the filament tapers within each of said bending curves continuously toward each narrowing, and wherein narrowings of each of said bending curves are arranged in a circumferential direction of the support prosthesis with respect to a longitudinal axis of said prosthesis exclusively on the inlet side or exclusively on the outlet side of the bending curves.

2. The support prosthesis according to claim 1, wherein the bending curves are free from portions having a constant cross-sectional area.

3. The support prosthesis according to claim 2, wherein the meandering pattern follows a helix path.

4. The support prosthesis according to claim 2, wherein the curvature of an inner curve and an outer curve within the bending curve has a continuous course.

5. The support prosthesis according to claim 1, wherein the support ring is expandable in the radial direction.

6. The support prosthesis according to claim 1, further comprising additional meandering patterns, the additional meandering patterns and the meandering pattern of the filament forming a plurality of meandering patterns, wherein adjacent meandering patterns of the plurality of meandering patterns are arranged phase-offset through 180°.

7. The support prosthesis according to claim 6, wherein the adjacent meandering patterns are connected by connecting elements arranged between adjacent bending curves of the adjacent meandering patterns.

8. The support prosthesis according to claim 7, wherein an even number of bending curves without connecting elements are located along a meandering pattern between bending curves with connecting elements.

9. The support prosthesis according to claim 1, wherein the meandering pattern is undulating in its configuration.

10. The support prosthesis according to claim 1, wherein the meandering pattern follows a helix path.

11. The support prosthesis according to claim 10, wherein the filament forming the meandering pattern forms a respective closed loop at the ends of the tubular casing.

12. The support prosthesis according to claim 1, wherein the curvature of an inner curve and an outer curve within the bending curve has a continuous course.

* * * * *